United States Patent [19]

Malchesky et al.

[11] 4,127,481
[45] Nov. 28, 1978

[54] DEVICE AND METHOD FOR EFFECTING FLUID INTERCHANGE FUNCTIONS

[75] Inventors: Paul S. Malchesky, Painesville Township, Lake County; Yukihiko Nose, Cleveland Heights, both of Ohio

[73] Assignee: Japan Foundation for Artificial Organs, Cleveland, Ohio

[21] Appl. No.: 867,089

[22] Filed: Jan. 5, 1978

Related U.S. Application Data

[63] Continuation of Ser. No. 672,720, Apr. 1, 1976, abandoned.

[51] Int. Cl.² ............... B01D 13/00; B01D 31/00
[52] U.S. Cl. .................... 210/22 A; 210/36; 210/321 R; 210/434; 128/214 B
[58] Field of Search ........... 210/321 R, 321 A, 321 B, 210/22, DIG. 23, 433 M, 36, 434; 128/214 B, 214 F

[56] References Cited

U.S. PATENT DOCUMENTS

| | | | |
|---|---|---|---|
| 2,683,117 | 7/1954 | Rosenak et al. | 210/321 A |
| 2,972,349 | 2/1961 | De Wall | 210/321 B |
| 3,228,877 | 1/1966 | Mahon | 210/22 |
| 3,342,729 | 9/1967 | Strand | 210/321 B |
| 3,608,729 | 9/1971 | Haselden | 210/321 B |
| 3,669,878 | 6/1972 | Marantz et al. | 210/321 B |
| 3,728,256 | 4/1973 | Cooper | 210/321 B |
| 3,734,298 | 5/1973 | Riede et al. | 210/321 B |
| 3,742,946 | 7/1973 | Grossman | 210/321 R |
| 3,746,176 | 7/1973 | Markley | 210/321 |
| 3,930,105 | 12/1975 | Christen et al. | 210/505 |
| 3,962,094 | 6/1976 | Dans et al. | 210/321 R |
| 4,013,564 | 3/1977 | Nose | 210/321 R |

OTHER PUBLICATIONS

Enzyme Engineering, Wingard, Jr., 1972, John-Wiley and Sons, pp. 123–144.
"Microemboli-Free Blood Detoxification Utilizing Plasma Filtration", Castino et al., Trans. ASAIO, vol. XXII, 1976, p. 637.

*Primary Examiner*—Frank A. Spear, Jr.
*Assistant Examiner*—David R. Sadowski
*Attorney, Agent, or Firm*—Baldwin, Egan, Walling & Fetzer

[57] ABSTRACT

Extracorporeal and implantable blood interchange devices used in providing interchange function of predetermined components with a fluid, such as for instance the removal of undesirable components from the bloodstream of a human and, characterized by capillary tubing having a reactor or sorbent material, such as activated charcoal, disposed within the lumens thereof, with the tubing being semi-permeable and with blood, or other fluid, being perfused over the capillary tubing in close physical contact with the exterior surfaces thereof, for accomplishing interchange coaction between the sorbent in the tubing and the perfusing fluid. Such tubing is arranged in rectangular configuration, with tangential entry and exit of perfused fluid.

21 Claims, 13 Drawing Figures

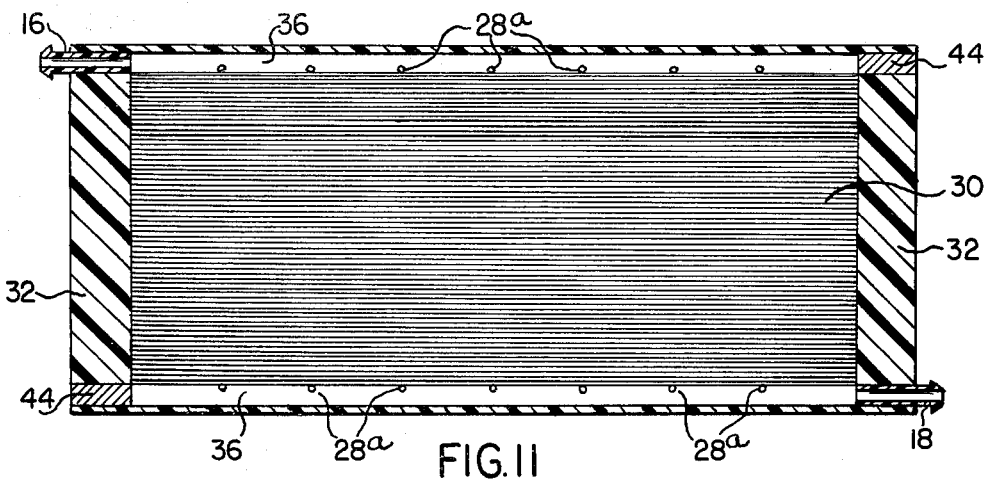
FIG.11
FIG.10
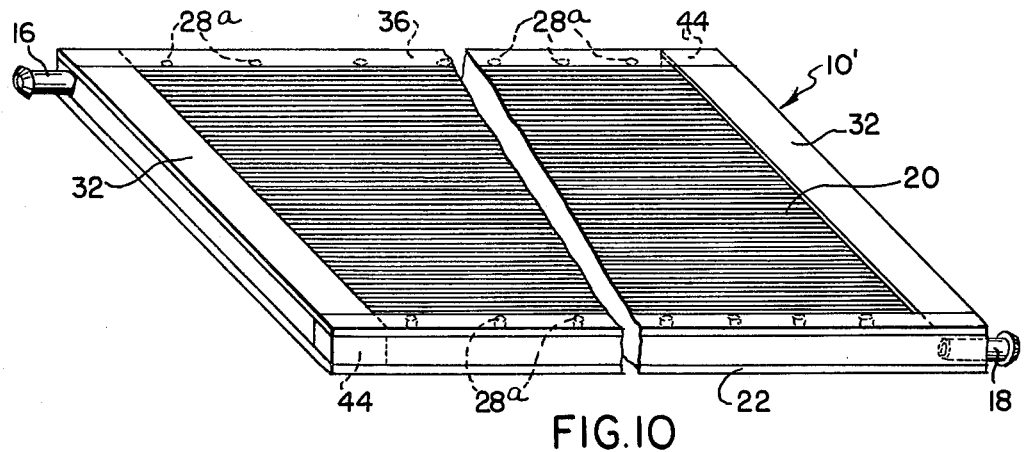
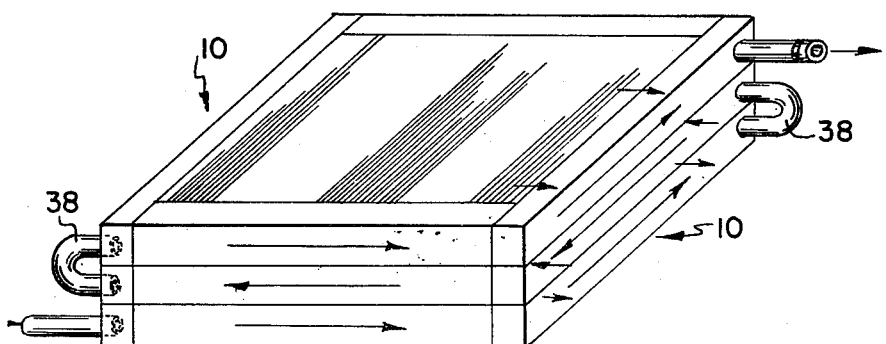
FIG.12
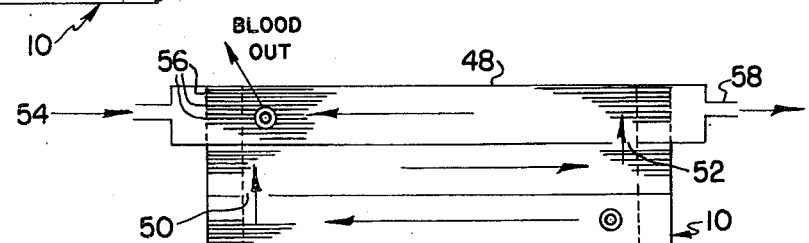
FIG.13

DEVICE AND METHOD FOR EFFECTING FLUID INTERCHANGE FUNCTIONS

This application is a continuation application of copending U.S. Ser. No. 672,720 in the name of Paul S. Malchesky and Yukihiko Nose filed Apr. 1, 1976 and entitled DEVICE AND METHOD FOR EFFECTING FLUID INTERCHANGE FUNCTIONS, now abandoned.

This invention relates to extracorporeal and/or implantable devices for effecting a fluid interchange function, such as for instance removal of undesirable components from blood or other fluid, and wherein the device includes capillary tubing means having a reactor or sorbent disposed therein, with the fluid being adapted to coact with the tubing means in close physical contact with the exterior surfaces thereof, for removal of designated components from the fluid for treatment of the latter, and particularly relates to a rectangular shaped device for removing undesirable components from blood.

BACKGROUND OF THE INVENTION

The use of sorbent devices and/or dialysis devices for the removal of undesirable components, such as toxic constituents in blood are known in the art. It is also known that activated carbon is an excellent sorbent for removing organic metabolic wastes, drugs and other undesirable components from the blood. However, because of its high affinity for blood components as platelets, and its tendency to fragment, activated carbon has to be isolated from direct contact with blood in a hemoperfusion circuit. It is known in the art to encapsulate activated carbon particles in a polymeric coating, utilizing fine particles of activated carbon. However, studies have indicated that even with coated sorbents, the problem of microemboli still exists, and is related apparently to the technique of coating, the fragility of the coating, and to the construction of the devices using the coated sorbents. Moreover, it is known to coat activated charcoal particles by dispersing them into a solution of a polymeric binder, and then spinning the dispersion into fiber. The fibers serve to immobilize the carbon and prevent direct contact between the carbon and the blood. A dispersion of the powder activated carbon in a solution of alkali hydroxyethylcellulose (HEC) is extruded through a spinneret into an acid bath to coagulate the HEC into regenerated filaments. Such filaments are wound on a perforated spindle and sealed in a cartridge housing, with blood to be cleansed being pumped through the perforated spindle over the HEC solid filaments, and then out of the housing.

Even though various schemes of coating of sorbents as discussed above have been employed, studies have shown that the coated sorbents still may involve a microemboli problem of the carry-over of emboli of the sorbent into the vascular system. Moreover, in these prior art devices, nondesired sorption of certain blood or fluid components sometime occurs, which is detrimental to certain physiologic functions.

SUMMARY OF THE INVENTION

The present invention embodies a device providing for interchange coaction with a fluid, such as for instance, a device for removing undesirable components from a fluid such as the bloodstream, and utilizing capillary tubing means with the tubing means being semi-permeable and having a sorbent disposed therein, with the fluid being adapted to flow around the closely spaced tubing means to cause removal of undesirable components from the blood.

Accordingly, an object of the invention is to provide a compact, portable device providing for effective interchange coaction with a fluid, such as for instance the bloodstream.

Another object of the invention is to provide a fluid interchange device which embodies semi-permeable capillary tubing arranged in rectangular configuration, having a reactor or sorbent disposed therein, and so constructed and arranged that the fluid coacts in an interchange relation with the sorbent or reactor material in the tubing as it flows over the exterior thereof.

Another object of the invention is to provide a device of the above type which is capable of relatively high volumetric flow and is sufficiently inexpensive that it may be employed as a disposable item.

Another object of the invention is to provide a device of the aforedescribed general type including a casing for receiving the tubing therein and wherein the casing is of rectangular configuration in plan, with the tubing being generally spaced and parallel extending.

Another object of the invention is to provide a fluid interchange device utilizing capillary tubing having a granulated charcoal disposed within the lumens of the tubing, and with the tubing being semi-permeable so that fluid passed over in close contact with the exterior surfaces of the tubing causes an interchange of designated components from the fluid to the charcoal.

A still further object of the invention is to provide a fluid interchange device embodying charcoal as a filtering element, and which eliminates the problem of microemboli, and providing a device which can be expeditiously used in conjunction with a dialysis device.

Another object of the invention is to provide a fluid interchange sorbent device in combination with a dialyzer.

Other objects and advantages of the invention will be apparent from the following description taken in conjunction with the accompanying drawings wherein:

FIG. 10 is a perspective, generally diagrammatic illustration of another structural embodiment of interchange device.

FIG. 11 is a horizontal sectional view (in plan) of a device of the type of FIG. 10.

FIG. 12 is a generally diagrammatic, perspective illustration of a stack of the interchange devices of the invention interconnected with one another for increasing the interchange capacity; and FIG. 13 is a diagrammatic illustration of a pair of interconnected interchange devices of the invention coacting with a dialyzer device, for expeditious removal of unwanted components from the bloodstream.

DESCRIPTION OF PREFERRED EMBODIMENTS

Figure 1:
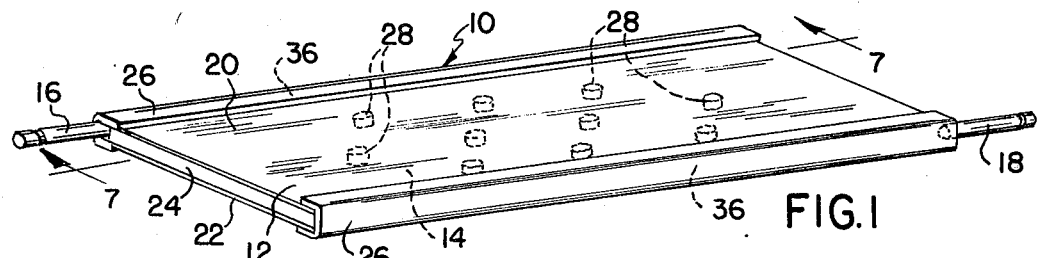
FIG. 1 is a perspective view of a fluid interchange device embodying the invention.

Referring now again to the drawings, there is illustrated a fluid interchange device 10 which comprises a rectangular casing 12 defining an interior cavity or chamber 14. An inlet tube 16 communicates with the interior of the chamber at one end of the casing and an outlet tube 18 communicates with the chamber at the diametrically opposite corner of the casing.

In the embodiment illustrated, the casing is formed of upper and lower monoplanar plates 20, 22 of polycarbonate sheet of approximately 0.040 inch (1mm) to ⅛ inch (1.6mm) thickness, with end plates or closures 24 (FIG. 1) and side rails 26, secured to one another to form fluid tight chamber 14. Strengthening rib means 28 (FIG. 1) may extend between the interior surfaces of the upper and lower plates 20, 22 and be secured thereto, for preventing flexure or ballooning of the plates under pressurized fluid load. The casing components 16, 18, 20, 22, 24 and 26 can be secured to one another by suitable adhesive means, such as for instance a suitable, known polyurethane compound, or by mechanical fastener means.

Figure 6:
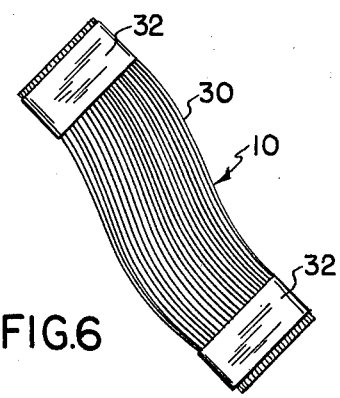
FIG. 6 is a reduced size generally top plan view of the subassembly of the capillary tubing having the sorbent disposed therein used in the device of FIG. 1 and showing the capillary tubing potted at its ends.

Disposed within the chamber 14 is capillary tubing means 30 (FIG. 6) having a sorbent 30a disposed within the lumens of the tubing. The sorbent presently used is activated powdered charcoal, adapted for the removal of drugs and organic solutes from the bloodstream, and is contained or encapsulated in the hollow tubing which is semi-permeable. The tubing may be formed of regenerated cellulose processes by a known process called the Cuproammonium Process. Such charcoal filled capillary tubing is commercially available from a German company identified as Enka Glanzstoff Ag of Werk Wuppertal-Barmen, Germany. Such membrane material is known by the trade name Cuprophan. Such a tubing product is hydrophilic and has a maximum pore diameter less than the minimum diameter of embolizing sorbent particles, and also a pore diameter less than the size of the cellular components of the fluid such as blood adapted for coaction therewith. Also, such tubing must have transfer characteristics which allow passage of solutes therethrough which are to be reacted with the filling material in the capillary tubing. Other membrane materials could be used such as synthetic or naturally occurring polymers as long as they meet the above criteria.

The casing 12 of the interchange device 10 must have adequate mechanical strength with dimensional changes, upon wetting thereof, being minimal. Also the chamber of the device must lend itself to sterilization and be free of pyrogen.

A suitable material for the casing 12 has been found to be polycarbonate although other polymeric films such as acrylic would also be suitable.

The sorbent filled tubing being used has characteristics nominally as follows:
Breaking load — 150 grams
Maximum elongation — 7%
Weight per thousand meters — 54 grams
External diameter, dry — 285 microns
Wall thickness — approximately 10 microns
Part by weight of activated charcoal —60%
Sorption rate of creatinine — 90 milligrams per gram carbon after 2 hours, at 37° C.

Figure 7:
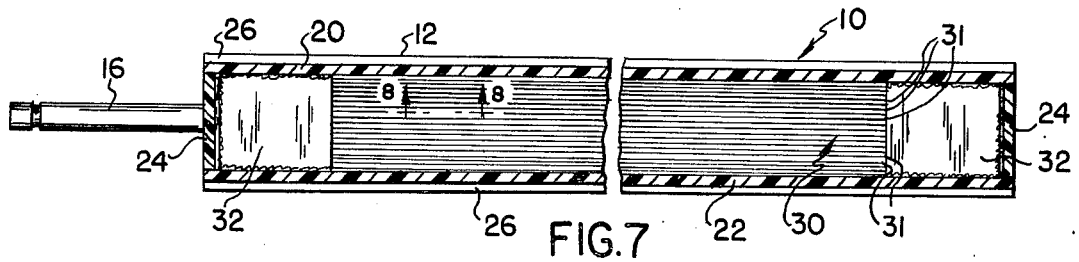
FIG. 7 is an enlarged, broken, sectional view taken generally along the plane of line 7—7 of FIG. 1 looking in the direction of the arrows.
Figure 8:
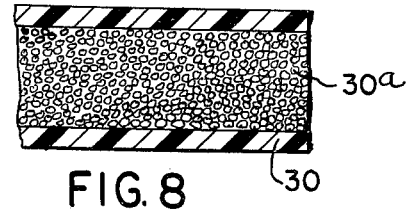
FIG. 8 is an enlarged, fragmentary, sectional view of one of the tubing elements showing the charcoal filling therein.

As an example of the structural and orientational arrangement of the capillary tubing 30, reference is made to FIG. 7 wherein layers 31 of the filled tubing elements are laid down using a lateral spacing of approximately 0.056 millimeters both vertically and horizontally. In order to maintain spacing between the tubing elements, the ends of the tubing elements are potted as at 32 (FIGS. 6 and 7) utilizing an adhesive such as a two part polyurethane adhesive as the potting material. An example of such adhesive is Vorite 689 and DB oil produced by N. L. Industries of New York. Maintenance of uniform spacing is deemed important in providing for controlled and uniform flow of fluid, such as blood, over and past the capillary tubing to permit interchange between the fluid and the sorbent in the tubing. The potted ends of the tubing are secured by the adhesive to the plates 20, 22 and the end closures 24, to maintain a generally parallel relation between the capillary tubing elements, which extend generally linearly in the chamber 14. Potting thus coats the end portions of the capillary tubing unit 30, and maintains the tubing elements in predetermined relation with respect to one another when such potted ends are secured in the casing 12. Potting or adhering of the ends of the tubing elements together may also be done directly in the case 12 rather than first potting the ends and then adhering the capillary tubing 30 as a unit in the case 12.

The aforementioned supports 28 used interiorly of the case 12 prevent expansion or ballooning of the casing during pumping (FIG. 9) or collapse during suction and also are adapted to prevent the tubing 30 from expanding into the manifold areas 36, of the interchange unit, and as best illustrated, for instance in FIGS. 10 and 11. Thus the potted tubing subassembly is assembled interiorly of the chamber in the casing with the ribs or pins 28 projecting upwardly through the layers of tubing when such ribs or pins are disposed intermediate the extremities of the capillary unit, and then the upper plate 20 is cemented or otherwise secured in place and to both the ribs or pins 28 and the potted ends 32 of the tubing 30, so as to maintain the integrity of the tubing assembly in the casing.

While only one casing member is illustrated, it will be understood that a plurality of the casing members could be coupled in series (the outlet of one to the inlet of another) and provide for the serial flow of blood through the various casings. An example of such an arrangement is illustrated in FIG. 12. While exterior tubing components 38 are illustrated for interconnecting the inlets and outlets of the stacked interchange units, the latter could be instead interconnected interiorly by suitable arrangement of the dividing plates. Parallel flow could also be achieved.

As an example of the preferred interior size of the casing, dimensions of approximately 24 cm. length, 10 cm. width and 6-7 mm. in thickness, have been successful. Actual choice of dimensions is a function of the number of capillaries or fibers used and the flow conditions required.

Figure 2:
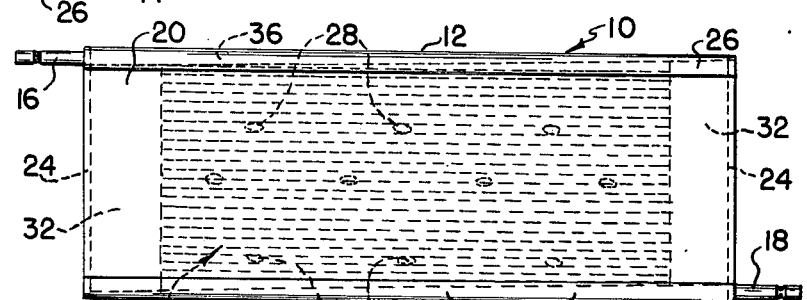
FIG. 2 is a top plan view of the device of FIG. 1.
Figure 4:
FIG. 4 is a sectional view taken generally along the plane of line 4—4 of FIG. 3 looking in the direction of the arrows.
Figure 3:
FIG. 3 is a side elevational view of one of the corner strips utilizing formation of the casing of the device of FIGS. 1 and 2.
Figure 5:
FIG. 5 is an elevational view of one of the inlet or outlet tubes of the device of FIG. 1.

With the rail arrangement 26 for closing the lengthwise sides of the device 10 of FIG. 1, the inlet and outlet tubes 16 and 18 can extend from between the arms of the respective rail 26 (as best shown in FIG. 1) and adjacent the respective potted end 32 of the tubing assembly. Accordingly, as can be seen in FIG. 2, the tubing assembly 30 may be slightly rotated counterclockwise in the chamber 14, resulting in clear space entry and exit manifold areas 36 (FIG. 2) running along the respective side of the tubing assembly, to facilitate inlet and egress movement of the fluid through the device.

In order to test a device of 34 gms. of activated charcoal, an artificial solution was made of standard dialysate solution (no glucose) to which urea, creatinine, and uric acid were added in the concentration of approximately 200 milligrams %, approximately 10 milligrams % and approximately 10 milligrams %, respectively. During the test, the solution was recirculated and maintained fully mixed. Pressure into and out of the device 10 was monitored, and the blood solution flow was maintained at 200 milliliters per minute during a 4 hour test.

In operation, the fluid enters the inlet tube 16, passes into the chamber space or entry manifold 36 along the side of the casing, and then flows uniformly over and around the tubing means 30 disposed in the casing to the outlet tube 18. In passing over the generally evenly spaced capillary tubing means, the fluid passes between the spaced layers of tubing and is effectively acted upon by the sorbent in the semi-permeable tubing, to remove undesirable components or the like from the fluid without being in direct contact with the latter. Entry and exiting of the fluid into and from the interchange device is essentially tangential.

The following table 1 outlines the mass transfer results obtained during the test. Clearance (C) of the table results is calculated as follows:

$$C = Q_b \times \left( \frac{C_b1 - C_b0}{C_b1} \right)$$

Where $Q_b$ is the fluid or blood solution flow in milliliters per minute; $C_b1$ is the inlet solution concentration in milligrams %; and $C_b0$ is the outlet solution concentration in milligrams %. Mass transfer parameter (MTP) was calculated as follows:

$$MTP = V_b \ln \left( \frac{C_b f}{C_b 1} \right) \times (T_f - T_1)$$

Where $V_b$ is the blood solution volume in milliliters; $C_b f$ is solute concentration at final time $T_f$, in minutes; and $C_b 1$ is the solute concentration at initial time $T_1$ in minutes. The mass transfer parameter for the 4 hour test was 76.7 milliliters per minute for uric acid and approximately 51.7 milliliters for creatinine.

TABLE I
SUMMARY OF MASS TRANSFER RESULTS ON DEVICE #C1

|  | CREATININE | | | URIC ACID | | |
|---|---|---|---|---|---|---|
| Sampling time | $C_{b_i}$ | $C_{b_o}$ | Clearance ML/min. | $C_{b_i}$ | $C_{b_o}$ | Clearance ML/min. |
| <30 minutes | 7.7 | 3.6 | 106 | 6.6 | 2.7 | 118 |
| 30 minutes | 7.3 | 4.0 | 90 | 6.0 | 2.8 | 110 |
| 60 minutes | 6.9 | 4.3 | 75 | 5.6 | 2.8 | 100 |
| 90 minutes | 6.6 | 4.4 | 67 | 5.2 | 2.8 | 92 |
| 120 minutes | 6.3 | 4.4 | 60 | 4.9 | 2.8 | 86 |
| 150 minutes | 6.0 | 4.5 | 50 | 4.5 | 2.8 | 76 |
| 180 minutes | 5.8 | 4.5 | 45 | 4.2 | 2.8 | 67 |
| 210 minutes | 5.6 | 4.5 | 39 | 4.0 | 2.8 | 60 |
| 240 minutes | 5.4 | 4.5 | 33 | 3.8 | 2.8 | 53 |

In an experimental setup similar to that previously described, test was made of a three-module unit containing 76.8 gms. activated carbon at a flow of 200 ml/min recirculated into a 34 liter bath of physiologic saline at 37° C. for four hours. Starting concentrations in the range of 8 mg% for creatinine and uric acid were used. The following tables 2, 3 and 4 outline the results of this study. At the termination of this study the pressure drop monitored as a function of solution flow rate was less than 30 mm Hg for flows up to 500 ml/min. Priming volume of the three-module system was 195 ml not including line volume. Total particle release as measured by the weight difference in a 0.22 micron Millipore filter before and after physiologic saline is circulated at 100 bed volumes was less than 1 mg when measured prior to any previous testing.

A third unit containing 37 gms. activated carbon was tested. The simulated blood solution (dialysate with no glucose) of 35 liters was recirculated at 200 ml/min (solution was drawn through device). The solution contained 9.4 mg% creatinine and 19.5 mg% salicylate as starting concentrations at pH 7.34. Final pH was 7.20. Particle release as measured by the weight difference in a 0.45 micron Millipore filter before and after saline flush was 1.7 mg. The following tables 5, 6 and 7 outline the mass transfer results on this device. Pressure drop of this device was under 220 mm Hg at a flow of 200 ml/min. Priming volume as determined at the end of the test was 45 ml.

TABLE 2

| | URIC ACID DATA FOR THREE MODULE SYSTEM (76.8g CHARCOAL) | | | | | | | |
|---|---|---|---|---|---|---|---|---|
| TIME | TOTAL $\frac{C_{B_i} - C_{B_0}}{C_{B_i}}$ | TOTAL CLEARANCE | 1st UNIT $\frac{C_{B_i} - C_{B_0}}{C_{B_i}}$ | 1st UNIT CLEARANCE | 2nd UNIT $\frac{C_{B_i} - C_{B_o}}{C_{B_i}}$ | 2nd UNIT CLEARANCE | 3rd UNIT $\frac{C_{B_i} - C_{B_o}}{C_{B_i}}$ | 3rd UNIT CLEARANCE |
| ½ hr. | $\frac{5.2}{6.3} = 0.825$ | 165 | $\frac{2.3}{6.3} = 0.365$ | 73.02 | $\frac{2.0}{4.0} = 0.5$ | 100 | $\frac{0.9}{2.0} = 0.45$ | 90 |
| 1 hr. | $\frac{4.3}{5.7} = 0.754$ | 150.9 | $\frac{1.7}{5.7} = 0.298$ | 59.65 | $\frac{1.5}{4.0} = 0.375$ | 75 | $\frac{1.1}{2.5} = 0.44$ | 88 |
| 1¼ hr. | $\frac{3.3}{4.9} = 0.673$ | 134.7 | $\frac{1.2}{4.9} = 0.245$ | 48.98 | $\frac{1.3}{3.7} = 0.35$ | 70.27 | $\frac{0.8}{2.4} = 0.333$ | 66.67 |
| 2 hr. | $\frac{2.9}{4.4} = 0.659$ | 131.8 | $\frac{1.0}{4.4} = 0.227$ | 45.45 | $\frac{1.0}{3.4} = 0.294$ | 58.8 | $\frac{0.9}{2.4} = 0.375$ | 75 |
| 3 hr. | $\frac{2.0}{3.7} = 0.54$ | 108 | $\frac{0.8}{3.7} = 0.216$ | 43.24 | $\frac{0.6}{2.9} = 0.207$ | 41.38 | $\frac{0.6}{2.3} = 0.261$ | 52.2 |

TABLE 2-continued

| | URIC ACID DATA FOR THREE MODULE SYSTEM (76.8g CHARCOAL) | | | | | | | |
|---|---|---|---|---|---|---|---|---|
| TIME | TOTAL $\dfrac{C_{B_i} - C_{B_0}}{C_{B_i}}$ | TOTAL CLEAR-ANCE | 1st UNIT $\dfrac{C_{B_i} - C_{B_0}}{C_{B_i}}$ | 1st UNIT CLEAR-ANCE | 2nd UNIT $\dfrac{C_{B_i} - C_{B_0}}{C_{B_i}}$ | 2nd UNIT CLEAR-ANCE | 3rd UNIT $\dfrac{C_{B_i} - C_{B_0}}{C_{B_i}}$ | 3rd UNIT CLEAR-ANCE |
| 4 hr. | $\dfrac{1.03}{2.83} = 0.364$ | 72.8 | $\dfrac{0.33}{2.83} = 0.117$ | 23.3 | $\dfrac{0.4}{2.5} = 0.16$ | 32 | $\dfrac{0.3}{2.1} = 0.143$ | 28.6 |

Uric Acid Starting Concentration 7.6 mg%
Total Volume 34 Liters at 37° C
Blood Solution Flow - 200ml/min
Test Duration - 4hrs.
Total Uric Acid Removed - 1.622g or 21.1mg Uric Acid/g Charcoal
Per Cent Removal - 62.7%

TABLE 3

| | CREATININE DATA FOR THREE MODULE SYSTEM (76.8g CHARCOAL) | | | | | | | |
|---|---|---|---|---|---|---|---|---|
| TIME | TOTAL $\dfrac{C_{B_i} - C_{B_0}}{C_{B_i}}$ | TOTAL CLEAR-ANCE | 1st UNIT $\dfrac{C_{B_i} - C_{B_0}}{C_{B_i}}$ | 1st UNIT CLEAR-ANCE | 2nd UNIT $\dfrac{C_{B_i} - C_{B_0}}{C_{B_i}}$ | 2nd UNIT CLEAR-ANCE | 3rd UNIT $\dfrac{C_{B_i} - C_{B_0}}{C_{B_i}}$ | 3rd UNIT CLEAR-ANCE |
| ½ hr. | $\dfrac{5.7}{7.4} = 0.77$ | 154.1 | $\dfrac{2.3}{7.4} = 0.311$ | 62.6 | $\dfrac{1.9}{5.1} = 0.373$ | 74.51 | $\dfrac{1.5}{3.2} = 0.469$ | 93.75 |
| 1 hr. | $\dfrac{4.4}{6.6} = 0.666$ | 133.33 | $\dfrac{1.7}{6.6} = 0.258$ | 51.5 | $\dfrac{1.5}{4.9} = 0.31$ | 61.2 | $\dfrac{1.2}{3.4} = 0.353$ | 70.6 |
| 1½ hr. | $\dfrac{3.7}{6.0} = 0.616$ | 123.33 | $\dfrac{1.4}{6.0} = 0.233$ | 46.66 | $\dfrac{1.1}{4.6} = 0.239$ | 47.8 | $\dfrac{1.2}{3.5} = 0.343$ | 68.6 |
| 2 hr. | $\dfrac{2.6}{5.3} = 0.49$ | 98.1 | $\dfrac{0.8}{5.3} = 0.151$ | 30.19 | $\dfrac{1.1}{4.5} = 0.244$ | 48.89 | $\dfrac{0.7}{3.4} = 0.206$ | 41.18 |
| 3 hr. | $\dfrac{1.8}{4.4} = 0.409$ | 81.82 | $\dfrac{0.3}{4.4} = 0.68$ | 13.66 | $\dfrac{0.9}{4.1} = 0.220$ | 43.90 | $\dfrac{0.6}{3.2} = 0.188$ | 37.5 |
| 4 hr. | $\dfrac{1.67}{3.97} = 0.421$ | 84.13 | $\dfrac{0.47}{3.97} = 0.118$ | 23.68 | $\dfrac{0.4}{3.5} = 0.114$ | 22.86 | $\dfrac{0.8}{3.1} = 0.258$ | 51.6 |

Creatinine Starting Concentration 8.45mg%
Total Volume 34 Liters at 37° C
Blood Solution Flow - 200ml/min
Test Duration - 4 hrs.
Total Creatinine Removed - 1.523g or 19.8mg Creatinine/g Charcoal
Percent Removal - 53%

TABLE 4

| | MASS TRANSFER PARAMETER (K') VALUES FOR THREE MODULE SYSTEM (76.8g CHARCOAL) | | | | | | | |
|---|---|---|---|---|---|---|---|---|
| | URIC ACID | | | | | | | |
| TIME | TOTAL $\dfrac{C_{B_i}}{C_{B_0}}$ | TOTAL K' | 1st UNIT $\dfrac{C_{B_i}}{C_{B_0}}$ | 1st UNIT K' | 2nd UNIT $\dfrac{C_{B_i}}{C_{B_0}}$ | 2nd UNIT K' | 3rd UNIT $\dfrac{C_{B_i}}{C_{B_0}}$ | 3rd UNIT K' |
| ½ hr. | 1.745 | 4.544 | 0.454 | 1.182 | 0.693 | 1.805 | 0.598 | 1.557 |
| 1 hr. | 1.404 | 3.656 | 0.354 | 0.922 | 0.470 | 1.224 | 0.580 | 1.510 |
| 1.5 hr. | 1.119 | 2.914 | 0.281 | 0.732 | 0.433 | 1.128 | 0.405 | 1.055 |
| 2 hr. | 1.076 | 2.802 | 0.258 | 0.672 | 0.348 | 0.906 | 0.470 | 1.224 |
| 3 hr. | 0.778 | 2.026 | 0.244 | 0.635 | 0.232 | 0.604 | 0.302 | 0.786 |
| 4 hr. | 0.452 | 1.177 | 0.124 | 0.323 | 0.174 | 0.453 | 0.154 | 0.401 |
| | CREATININE | | | | | | | |
| ½ hr. | 1.471 | 3.831 | 0.372 | 0.969 | 0.466 | 1.214 | 0.633 | 1.648 |
| 1 hr. | 1.099 | 2.862 | 0.298 | 0.776 | 0.365 | 0.951 | 0.435 | 1.133 |
| 1.5 hr. | 0.959 | 2.497 | 0.266 | 0.693 | 0.273 | 0.711 | 0.420 | 1.094 |
| 2 hr. | 0.674 | 1.755 | 0.164 | 0.427 | 0.280 | 0.729 | 0.231 | 0.602 |
| 3 hr. | 0.526 | 1.370 | 0.071 | 0.185 | 0.248 | 0.646 | 0.208 | 0.542 |
| 4 hr. | 0.546 | 1.422 | 0.126 | 0.328 | 0.121 | 0.315 | 0.298 | 0.776 |

$$Q_B \dfrac{(C_{B_i} - C_{B_0})}{C_{B_i}} = KA\Delta C = K'm\Delta C \quad \text{m is mass of charcoal in g}$$

$$\Delta_C = \dfrac{(C_{B_i} - C') - (C_{B_0} - C')}{\ln \dfrac{C_{B_i} - C'}{C_{B_0} - C'}} \quad \text{C' effective concentration in charcoal, C' from isotherm is zero}$$

TABLE 5

| CREATININE DATA FOR UNIT 04 (37g CHARCOAL) | | |
|---|---|---|
| TIME | $\dfrac{C_{B_i} - C_{B_0}}{C_{B_i}}$ | CLEARANCE ml/min |
| ½ hr. | $\dfrac{3.5}{8.8} = 0.398$ | 79.6 |
| 1 hr. | $\dfrac{3.8}{8.3} = 0.458$ | 91.6 |
| 1½ hr. | $\dfrac{2.1}{7.5} = 0.280$ | 56.0 |
| 2 hr. | $\dfrac{2.4}{7.4} = 0.324$ | 64.8 |
| 3 hr. | $\dfrac{1.6}{6.7} = 0.239$ | 47.8 |

TABLE 5-continued
CREATININE DATA FOR UNIT 04 (37g CHARCOAL)

| TIME | $\dfrac{C_{B_i} - C_{B_o}}{C_{B_i}}$ | CLEARANCE ml/min |
|---|---|---|
| 4 hr. | $\dfrac{1.47}{6.57} = 0.224$ | 44.7 |

Creatine Starting Concentration 9.4mg%
Total Volume 34 Liters at 37° C
Blood Solution Flow - 200ml/min
Test Duration - 4 hrs.
Total Creatinine Removed - 0.9622g or 26.0mg Creatinine/g Charcoal
Percent Removal - 30.1%

TABLE 6
SALICYLATE DATA FOR UNIT 04 (37g CHARCOAL)

| TIME | $\dfrac{C_{B_i} - C_{B_o}}{C_{B_i}}$ | CLEARANCE ml/min |
|---|---|---|
| ½ hr. | $\dfrac{8.4}{18.4} = 0.413$ | 82.6 |
| 1 hr. | $\dfrac{8.2}{17.4} = 0.471$ | 94.2 |
| 1½ hr. | $\dfrac{5.5}{16.0} = 0.344$ | 68.8 |
| 2 hr. | $\dfrac{5.4}{15.5} = 0.348$ | 69.6 |
| 3 hr. | $\dfrac{3.8}{14.5} = 0.262$ | 52.4 |
| 4 hr. | $\dfrac{2.13}{13.43} = 0.159$ | 31.8 |

Salicylate Starting Concentration 19.5mg%
Total Volume 34 Liters at 37° C
Blood Solution Flow - 200ml/min
Test Duration - 4 hrs.
Total Salicylate Removed - 2.064g or 55.8mg Salicylate/g Charcoal
Percent Removal - 31.1%

| Time | mg adsorbed | $\dfrac{\text{Creatinine mg adsorbed}}{\text{g. carbon}}$ |
|---|---|---|
| ½ hr. | 204 | 5.51 |
| 1 hr. | 374 | 10.11 |
| 1½ hr. | 646 | 17.46 |
| 2 hr. | 680 | 18.38 |
| 3 hr. | 918 | 24.81 |
| 4 hr. | 962 | 26.00 |
|  |  | Salicylate |
| ½ hr. | 374 | 10.11 |
| 1 hr. | 714 | 19.30 |
| 1½ hr. | 1190 | 32.16 |
| 2 hr. | 1360 | 36.76 |
| 3 hr. | 1700 | 45.95 |
| 4 hr. | 2064 | 55.78 |

While activated charcoal particles have been found to be a highly useful sorbent for filling the lumens of the tubing section of the interchange device, there are other sorbents capable of use for removing toxin solutes in the bloodstream of a patient with renal failure, and as for instance zirconium oxide, zirconium phosphate, aluminum oxide. Enzymes, such as urease, might also be utilized.

Figure 9:
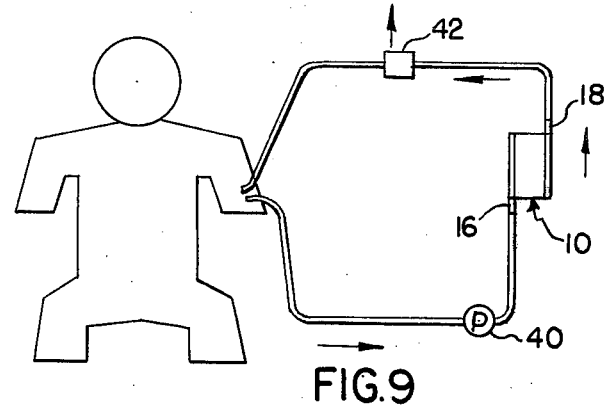
FIG. 9 is a diagrammatic illustration of the device of FIG. 1 coupled into a flow circuit which is hooked into the bloodstream of a mammal.

FIG. 9 illustrates an interchange device of the invention in a typical hemodialysis circuit, and including a blood pump 40, and a bubble trap 42.

FIGS. 10 and 11 illustrate a slightly modified embodiment 10' including filler sections 44 for maintaining the inlet and outlet manifolds 36 of generally uniform width longitudinally thereof for facilitating the flow characteristics of the device. In this embodiment, the pins or ribs 28 restrain the capillary tubing in use from expanding laterally into the manifold passages 36.

FIG. 12 illustrates an interconnected multilayer device, each layer of which can incorporate the same sorbent, or which may embody different reactors in the layers for the purpose of increasing the efficiency of the system or effecting various reactions on solute removal in the different layers.

FIG. 13 illustrates a dialyzing compartment 48 communicating with a pair of stacked capillary interchange devices 10, which communicate interiorly thereof by port 50 with one another, for the flow path of the blood or other fluid, and which communicate at port 52 with the dialyzing compartment 48. Dialysate is inserted at 54, passes through conventional tubular membranes 56, whereby cleansing of the blood occurs, and then the dialysate is removed at port 58.

From the foregoing discussion and accompanying drawings, it will be seen that the invention provides a novel device and method for effecting fluid interchange or like functions, and providing an interchange device which embodies capillary tubing means having a reactor or sorbent disposed therein, with the tubing means being semi-permeable to permit interchange coaction between the sorbent in the tubing means and the fluid which flows around and over the tubing means. The invention also provides a device of the aforediscussed type which is of rectangular configuration in plan and which is highly compact and lightweight and which is effective to provide for interchange coaction between the fluid and the sorbent or other material in the device.

The terms and expressions which have been used are used as terms of description and not of limitation, and there is no intention in the use of such terms and expressions of excluding any equivalents of any of the features shown or described, or portions thereof, and it is recognized that various modifications are possible within the scope of the invention claimed.

What is claimed is:

1. A device for effecting fluid interchange functions or the like including a substantially rigid casing defining an interior cavity, inlet means for fluid into said cavity, and outlet means for fluid from said cavity, capillary tubing means comprising a plurality of strands of capillary tubing having a particulate solid sorbent disposed therein within the lumen of the respective strand, said strands being anchored in said cavity, said tubing means being semi-permeable to permit interchange coaction between the sorbent in the tubing means and fluid adapted to flow into said inlet around the exteriors and not through said tubing means and from said outlet, said tubing means having a maximum pore diameter less than the minimum diameter of the sorbent particles and a pore diameter substantially less then the size of cellular components of the fluid, and having transfer characteristics which are non-plasma generating but which do allow passage of solutes therethrough for transfer reaction with said sorbent, manifold areas in said cavity on opposite sides of said capillary tubing means extending generally parallel to the direction of extension of said capillary tubing means, said inlet and said outlet opening into a respective of said manifold areas and in a direction generally parallel to the direction of extension of said tubing means and said manifold areas.

2. A device in accordance with claim 1 wherein said casing is of rectangular configuration in plan providing said cavity with a generally rectangular parallelepiped configuration, with said inlet being disposed adjacent one corner thereof and said outlet being disposed on an opposed side thereof, the fluid flow into said inlet and from said outlet being adapted to be substantially tangential with respect to the lengthwise extension of said tubing means and being generally crosswise of said tubing means between said inlet and said outlet in said cavity.

3. A device in accordance with claim 1 wherein said casing comprises generally flat laterally spaced parallel extending plastic panel structure and spaced strengthening rib means connecting the interior surfaces of said panel structure together, and holding and maintaining said panel structure in predetermined spaced relationship during flow of fluid through said cavity, for aiding in maintaining the generally rigid characteristic of said cavity.

4. A device in accordance with claim 3 wherein said casing is of rectangular configuration in plan providing said cavity with a generally rectangular parallelepiped configuration, said casing being formed of polymeric material, said inlet being disposed adjacent one corner of said casing and said outlet is disposed adjacent a diametrically opposite corner, said inlet and said outlet extending in generally lengthwise direction of extension of said capillary tubing strands, said rib means being disposed adjacent said opposite sides of said tubing means and restraining said tubing means from expanding laterally into said manifold areas during passage of fluid into said inlet and from said outlet, said tubing means being generally centrally located in said cavity lengthwise thereof and occupying substantially the full extent of spacing between said panel structure.

5. A device in accordance with claim 4 wherein said casing is formed of polycarbonate plastic.

6. A device in accordance with claim 1 wherein said casing is substantially a rectangular parallelepiped comprising monoplanar plastic sheets spaced laterally with respect to one another, channel-shaped rails coacting with at least certain of the edges of said sheets and forming the respective sides of the casing cavity, and means securing the rails to said sheets, said cavity being of substantially a rectangular parallelepiped configuration, said tubing means extending lengthwise of said cavity and being anchored adjacent the ends thereof to at least certain of the interior surfaces of said casing, said inlet being disposed adjacent one corner of said cavity and said outlet being disposed adjacent a diametrically opposite corner of said cavity, said inlet and said outlet extending in the general direction of extension of said tubing means, and opening into said spaced manifold areas in said cavity on opposite sides of said tubing means, said manifold areas extending lengthwise of said casing for the major portion of the lengthwise extension of said tubing means.

7. A device in accordance with claim 1 wherein said plurality of strands of semi-permeable capillary tubing are potted at the ends thereof in a plastic header, and with the sorbent in the tubing means comprising powered charcoal, said casing being a substantially rectangular parallelepiped and providing said cavity with a generally corresponding configuration, said potted ends of said capillary tubing being secured to interior defining surfaces of said cavity with said tubing extending lengthwise in the general lengthwise direction of extension of said cavity, said inlet being disposed adjacent one corner of said casing and said outlet being disposed adjacent a diametrically opposite corner, and opening into said spaced manifold areas in said cavity extending for substantially the full lengthwise extent of said tubing means.

8. A device in accordance with claim 7 wherein said tubing strands are laterally spaced generally uniformly with respect to one another at said potted ends a predetermined distance whereby fluid flow such as blood flow past the tubing means is of film-like nature so as to expose as much of the blood flow as possible to the action of the sorbent in the semi-permeable tubing means.

9. A device in accordance with claim 7 wherein the weight of each of the said strands is composed of approximately 60% by weight of the sorbent.

10. A device in accordance with claim 1 wherein said tubing means is potted at its ends in a plastic material and with said potted ends being secured to the interior of said casing by said plastic material so as to maintain the position integrity of the tubing means during flow of fluid through said casing, said casing being a generally flat rectangular parallelepiped providing said cavity with a generally corresponding configuration, said tubing means extending generally lengthwise of said cavity and with said strands of semi-permeable capillary tubing being thin walled and generally uniformly laterally spaced with respect to one another a predetermined distance at said potted ends whereby blood flow past the tubing strands is of film-like nature, thereby exposing as much of the blood flow as possible to the action of the sorbent in the semi-permeable tubing strands, said inlet being disposed adjacent one corner of said casing and said outlet being disposed adjacent a diametrically opposite corner of said casing, said inlet and outlet opening into respective of said spaced manifold areas in said cavity, said inlet and said outlet extending in the general direction of extension of said manifold areas, said strands of tubing occupying substantially the full extent of the flat dimension of said casing cavity.

11. A device in accordance with claim 1 wherein said device comprises a plurality of said casings, said plurality of casing communicating with one another so that fluid such as blood supplied to said inlet of one of said casings flows through all of said casings to the outlet of another of said casings of said device.

12. A device in accordance with claim 2 in combination with a dialyzing unit through which the fluid flows in series with said device.

13. An extracorporeal or implantable device for use in effecting blood interchange function including a generally rigid casing of rectangular parallelepiped configuration defining an interior cavity of generally flat rectangular parallelepiped configuration constituting a blood flow passage, an inlet for blood flow to said cavity, an outlet for blood flow from said cavity, capillary tubing means having potted ends anchored in said cavity intermediate said inlet and said outlet and defining a filter through which the blood flows from said inlet to said outlet thereof, and over the exterior of said capillary tubing means, said tubing means having a solid sorbent such as powdered activated charcoal, disposed therein within the lumens thereof and being semi-permeable for subjecting the blood flow to the cleansing function of the encompassed sorbent in said lumens, said tubing having a maximum pore diameter less than the minimum diameter of sorbent particles, and a pore diameter substantially less than the size of the cellular components of the blood, said tubing being formed of Cuprophan and having a wall thickness of approximately 10 microns, said inlet communicating with a manifold space running lengthwise of said cavity on one side of said tubing means and said outlet communicating with a manifold space running lenthwise of said cavity on the other side of said tubing means, said inlet and outlet extending in the general direction of extension of said manifold spaces whereby the blood flow into said inlet and from said outlet is substantially tangential with respect to the lengthwise extension of said tubing means, the blood flow being generally crosswise of said tubing means in said cavity intermediate said inlet and said outlet, said tubing means comprising a plurality of strands of semi-permeable capillary tubing generally uniformly spaced a predetermined distance with respect to one another at the potted ends thereof whereby blood flow past the tubing means is of film-like nature exposing as much of the blood flow as possible to contact with the sorbent encasing tubing, said tubing means having transfer characteristics which are non-plasma generating but which do allow passage from the blood of solutes therethrough for removal by said sorbent, said tubing means occupying substantially the full extent of the flat dimension of said cavity, and means extending in the direction of the flat dimension between interior surfaces of said cavity and aiding in preventing expansion of the tubing means into said manifold spaces.

14. A device for use in effecting fluid interchange functions or the like including a generally rigid casing defining an interior cavity of substantially rectangular parallelepiped configuration, inlet means for fluid into said cavity and outlet means for fluid from said cavity adjacent a corner thereof, capillary means including a particulate solid sorbent disposed interiorly of the lumens of the capillary means, anchored in said cavity at the ends thereof, said capillary means being semi-permeable and relatively thin walled to permit good contact by the sorbent encasing capillary means and fluid adapted to flow into said inlet past the exterior of said capillary means and from said outlet, said tubing means having a maximum pore diameter less than the minimum diameter of the sorbent particles and a pore diameter substantially less than the size of cellular components of the fluid and having transfer characterisitics which are non-plasma generating but which do allow passage of solutes therethrough for sorption by said sorbent, manifold areas in said cavity on opposite sides of said tubing means extending generally parallel to the direction of extension of said tubing means, said inlet and outlet means opening into a respective of said manifold areas and in a direction generally parallel to the direction of extension of said tubing means and said manifold areas, said inlet and outlet means and said manifold areas being so arranged with respect to said capillary means that the fluid flow into and from said casing will be substantially tangential with respect to the lengthwise extension of said capillary means, said capillary means comprising a plurality of strands of capillary tubing extending lengthwise of said cavity and the fluid flow intermediate said inlet and said outlet adapted to be generally transverse of said capillary means.

15. A method for effecting interchange functions between a fluid and a solid sorbent comprising providing a device having a closed generally rigid cavity of generally rectangular parallelepiped configuration, with an inlet for fluid and an outlet for fluid into and from said cavity, and with layers of spaced semi-permeable tubing means having a particulate solid sorbent disposed therein extending lengthwise of said cavity and anchored in said cavity adjacent the ends thereof, said solid absorbent being disposed within the lumens of the respective strands of tubing, said tubing means being semi-permeable to permit interchange coaction between the sorbent in the tubing means and fluid adapted to flow into said inlet around the exteriors of and not through said tubing means and from said outlet, said tubing means having a maximum pore diameter less than the minimum diameter of the sorbent particles and a pore diameter substantially less than the size of cellular components of the fluid and having transfer characteristics which are non-plasma generating but which do allow passage of solutes therethrough for transfer reaction with the sorbent, manifold areas in said cavity on opposites sides of said tubing means extending generally parallel to the direction of extension of said tubing means, said inlet and said outlet opening into a respective of said manifold areas in a direction generally parallel to the direction of extension of said tubing means, and then passing fluid into said inlet and the associated manifold area, then generally transversely around the exteriors of said tubing means to the other of said manifold areas, and then out said outlet, to cause interchange coaction between the sorbent in the tubing means and solutes in the fluid.

16. A method in accordance with claim 15 wherein the fluid flow is passed through said device via said inlet and said outlet and thence through a dialzying unit, while dialyzing fluid is passed through the lumen of the tubing of the dialyzing unit.

17. A method in accordance with claim 15 wherein said inlet is disposed at one corner of said cavity and said outlet is disposed adjacent a diametrically opposite corner, the fluid flow at said inlet and at said outlet is substantially tangential with respect to said tubing means, the latter being anchored at its ends to the interior surfaces of said cavity, said tubing means being formed of cellulose and being relatively thin walled of approximately 10 microns in wall thickness and with the solid absorbent comprising activated charcoal particles, and including providing the tubing means of a characteristic wherein the solid absorbent is approximately 60% by weight of the tubing means, and passing the fluid at said inlet and withdrawing substantially the same volume of fluid at said outlet into and from manifold areas in said cavity running lengthwise substantially the full lengthwise extent of said tubing means on opposite sides thereof.

18. A method in accordance with claim 15 wherein said tubing means are anchored at its ends in said cavity to aid in maintaining generally uniform spacing between said layers, and including restraining outward bulging of the tubing means and maintaining substantially tangential flow of the fluid with respect to the tubing means at said inlet and said outlet.

19. A method in accordance with claim 15 including providing a plurality of said devices and communicating the cavities thereof with one another so that the fluid supplied to the inlet of the first device will flow through all of the devices to the outlet of the last of the devices.

20. A device in accordance with claim 1 wherein said tubing is formed of cellulose processed by the Cuproammonium Process, and known as Cuprophan.

21. A device in accordance with claim 7 wherein said plastic header is comprised of a two part polyurethane adhesive.

* * * * *